Figure 1:
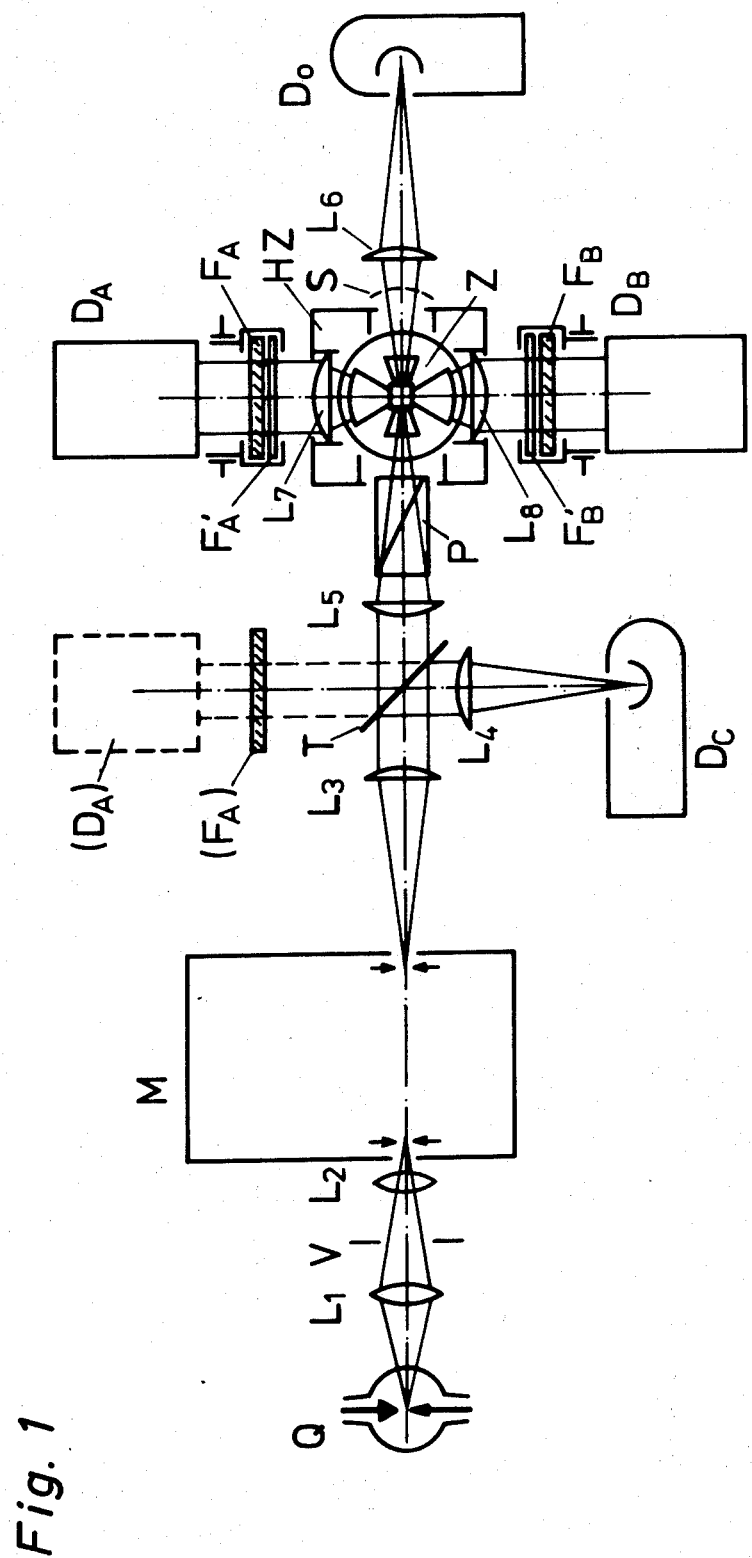

United States Patent [19]

Rabl et al.

[11] 3,972,627
[45] Aug. 3, 1976

[54] APPARATUS FOR INVESTIGATING FAST CHEMICAL REACTIONS BY OPTICAL DETECTION

[75] Inventors: Carl-Roland Rabl, Gottingen, Germany; Rudolf Rigler, Stockholm-Danderyd, Sweden; Thomas J. Jovin, Schloss Berlepsch, Germany; Hermann Bründl, Bodenfelde, Germany; Wolfgang Simm, Rosdorf, Germany

[73] Assignee: Max-Planck-Gesellschaft zur Forderung der Wissenschaften e.V., Gottingen, Germany

[22] Filed: July 11, 1974

[21] Appl. No.: 487,592

[30] Foreign Application Priority Data
Dec. 19, 1973 Germany............................ 2363180

[52] U.S. Cl............................. 356/246; 250/428; 250/565; 250/576; 356/104
[51] Int. Cl.² ......................................... G01N 21/24
[58] Field of Search ............ 356/244, 246, 96, 103, 356/104, 181; 250/428, 432, 564, 565, 573–576

[56] References Cited
UNITED STATES PATENTS

| | | | |
|---|---|---|---|
| 3,030,280 | 4/1962 | Miller | 204/195 T |
| 3,504,183 | 3/1970 | Salkowski et al. | 356/103 |
| 3,573,470 | 4/1971 | Haley | 356/208 |
| 3,610,757 | 10/1971 | Van Valkenburg | 356/244 |
| 3,679,309 | 7/1972 | Hiragaki et al. | 356/114 |
| 3,811,780 | 5/1974 | Liston | 356/244 |

OTHER PUBLICATIONS

Czerlinski, G., "Versatile Temperature Jump Apparatus for Following Chemical Relaxations", *Review of Scientific Instruments*, vol. 33, No. 11, Nov., 1962.
French et al., "Fast Reactions", *Methods in Enzymology*, vol. 16, ed. K. Kustin, Academic Press, N.Y. 1969 p. 21.
Hames, G. G., "Temperature–Jump Methods", *Techniques of Chemistry*, vol. 6, part 2, ed. A. Weissberger, Wiley Press, N.Y. 1974, pp. 153–155.

*Primary Examiner*—John K. Corbin
*Assistant Examiner*—Richard A. Rosenberger
*Attorney, Agent, or Firm*—Flynn and Frishauf

[57] ABSTRACT

An apparatus for investigating the course of fast chemical reactions, which are initiated in a liquid chemical system under investigation by an external perturbation, e.g. a steep temperature rise (temperature jump). The apparatus comprises first and second light paths conveying a probing light beam and a sense light beam, respectively, and an optical system of extremely high aperture which allows a wide variety of types of measurements, including absorption, fluorescense, fluorescense polarization, and the like with a high signal-to-noise ratio even of small sample concentrations.

15 Claims, 15 Drawing Figures

3,972,627

APPARATUS FOR INVESTIGATING FAST CHEMICAL REACTIONS BY OPTICAL DETECTION

BACKGROUND OF THE INVENTION

The present invention relates to an apparatus for investigating the kinetics of fast chemical reactions in solution using the temperature-jump-relaxation method with spectrophotometric observation of the time course of the reaction with special attention to the fluorimetric technique.

In conventional temperature-jump measurements a sample solution comprising a chemical system under investigation is filled into an optical sample cell having a volume of a few cubic centimeters. The cell is placed in the absorption light path of a spectrophotometer. The equilibrium parameters of the chemical system are changed by a stepwise increase of the temperature ("temperature jump"). Characteristic changes of the absorption spectrum after the temperature-jump indicate how fast the chemical system attains a new equilibrium state and the extent of the concentration changes of the reactants and reaction products. Usually, the temperature-jump is produced by discharging a high-voltage capacitor charge through the electrically conducting sample. To permit such a discharge, the sample cell has two electrodes made of noble metal or stainless steel forming a gap which is perpendicular to the light path. The discharge time and thus the heating time are of the order of 1 microsecond. The temperature change is several degrees centigrade. (C.F. M. Eigen et al. in: Zeitschr. f. Elektrochemie, Vol. 62, p. 652 (1959), M. Eigen and L. De Maeyer in: Technique of Organic Chemistry, Ed. A. Weissberger, Vol. 8/II, p. 895, Wiley, N.Y. 1963.) Known modifications of the temperature-jump technique use either the cable discharge method or heating by a microwave or infrared-laser pulse.

At low concentrations, and thus low optical absorption, the measurement of the concentration changes by means of absorption becomes difficult. On the other hand, the concentrations cannot be chosen arbitrarily with respect to the equilibrium constant of the chemical system under investigation. If the equilibrium constant of a first order reaction is very large, a temperature-jump experiment only leads to a significant displacement of the equilibrium at low concentrations. This is especially true for many biochemical reactions where the substances involved are active at extremely low concentrations. Furthermore, the costs of material preparation are of importance in biochemical studies. Thus it is of special interest to perform measurements using very small samples and low concentrations. It is also important to improve the specificity of the spectrophotometric detection method.

In the case of static spectrophotometers an improved high sensitivity at low concentrations as well as a high specificity can be achieved by measuring the fluorescence light which is emitted by many organic molecules when excited by light of shorter wavelength, especially ultraviolet light.

Temperature-jump measurements using fluorescence detection involve extremely difficult problems. The signal-to-noise-ratio is proportional to the square root of the light intensity divided by the signal risetime. The signal risetime of static spectrophotometers is of the order of 1 second. For microsecond temperature-jump measurements of small differential effects the light intensity should be $10^6$ times higher than with static measurements. The most obvious way to obtain a higher light intensity would be to use extremely powerful high-pressure lamps and monochromators. This possibility, however, is limited for chemical reasons, because of the finite photochemical stability of the sample, and for physical reasons, because the highest light intensities cannot be obtained without a decrease in light stability which is also very important for a high-resolution instrument. Due to these difficulties temperature-jump measurements using fluorimetric detection have only been successful in a few cases so far. At low concentrations the signal was lost in the noise.

OBJECTS AND SUMMARY OF THE INVENTION

It is therefore an object of the invention to produce temperature-jump signals of high quality even if small volumes and low concentrations are used. It is further an object of the invention to provide for an apparatus which allows to perform investigations of many different types with the same sample under reproducable and similar conditions. According to the invention, the sensitivity of a temperature-jump apparatus for fluorimetric measurements is considerably increased by using an immersion lens system in the emission light path. This lens system has an extremely high optical efficiency that exceeds the efficiency of commercial static fluorimeters by orders of magnitude. It is used together with other devices some of which are already known. The high optical efficiency of the measuring arrangement also makes feasible measurements of fluorescence polarization by optional insertion of polarizing elements in the light path. Losses of light cannot be avoided in this case but valuable additional information can be obtained, especially for studying binding of macromolecular substances. The instrument is also adapted for measurements of absorption. Thus comparative measurements of absorption, fluorescence and fluorescence polarization can be performed. Measurements of scattered light at an angle of 90° instead of fluorescence are also possible.

FIG. 1: Schematic diagram of the optical arrangement of the new apparatus.

FIGS. 2a to d: Vertical cross sections and horizontal cross section of a sample cell Z used in the arrangement according to FIG. 1.

FIGS. 2e and 2f: Horizontal cross sections of modified sample cells.

Figures 3, 4:
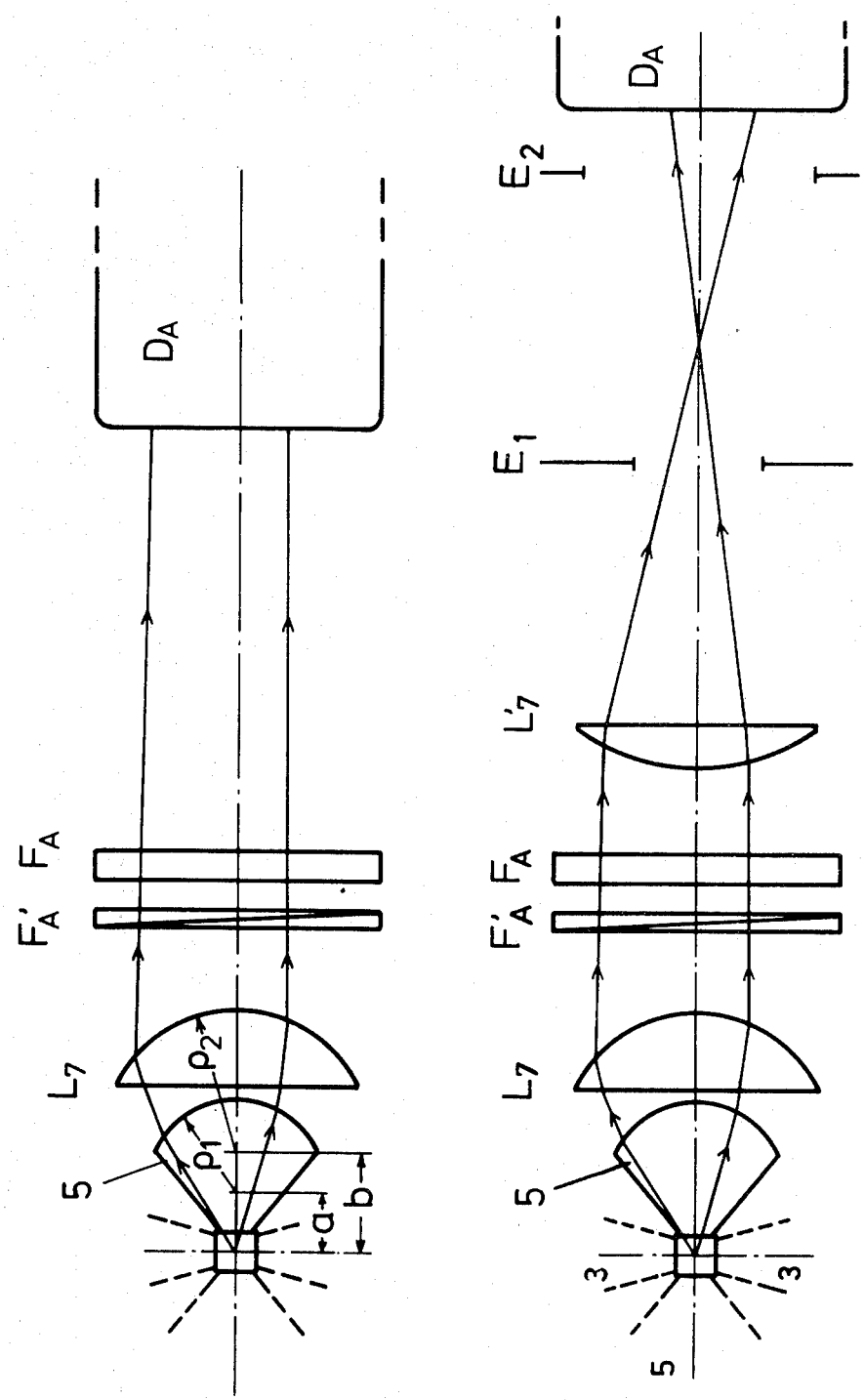

FIG. 3: Detailed drawing of the emission light path according to FIG. 1 and arrangement of an immersion lens system of extremely high optical efficiency each of which consists of one spherically ground cell window 5 and one lens $L_7$ ($L_8$) mounted in the cell holder HZ.

FIG. 4: Modified version of the lens system shown in FIG. 3 used to obtain an intermediate image of the sample cell volume.

Figure 5:
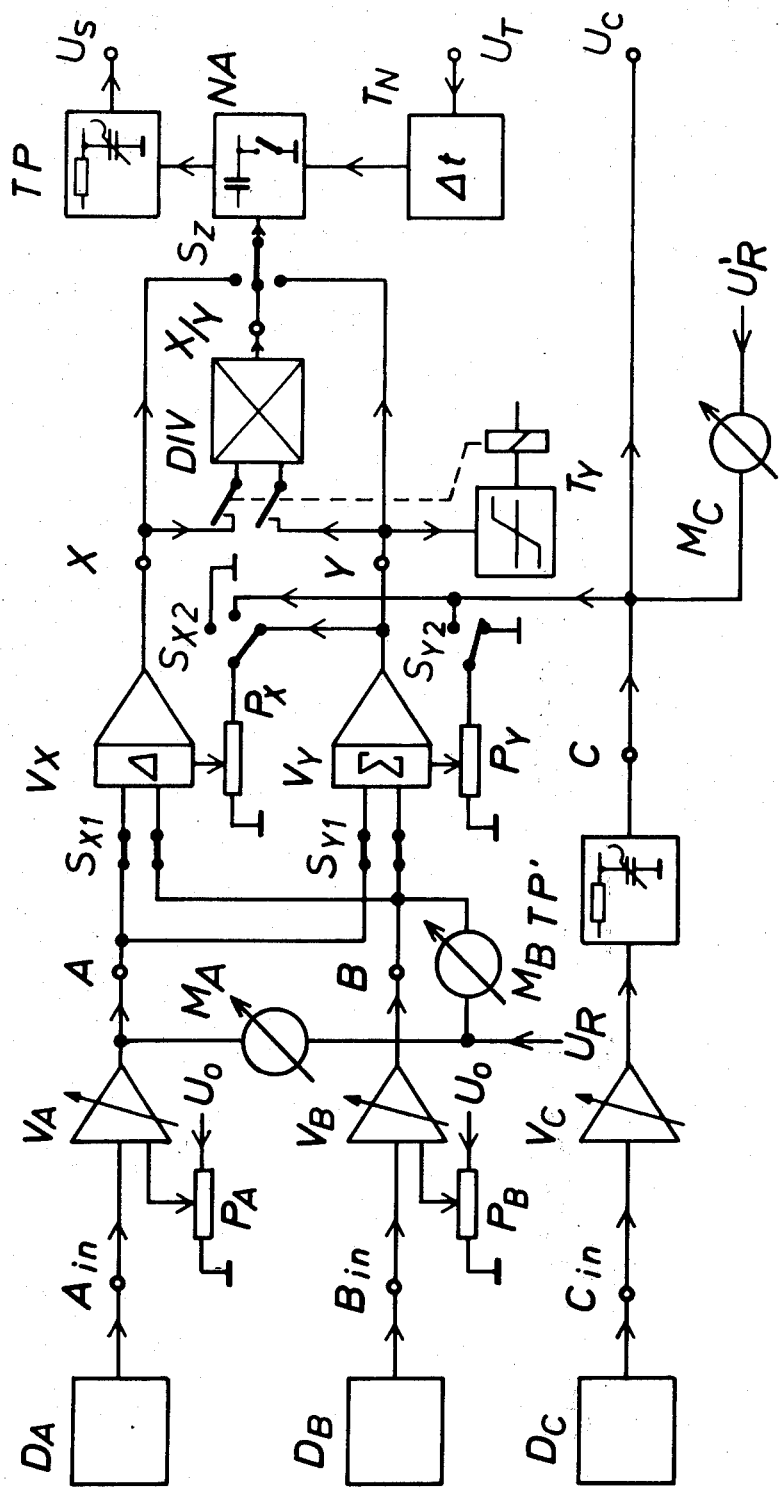

FIG. 5: Block diagram of an opto-electronic control unit for processing of the photodetector signals obtained by the arrangement shown in FIG. 1.

Figure 6:
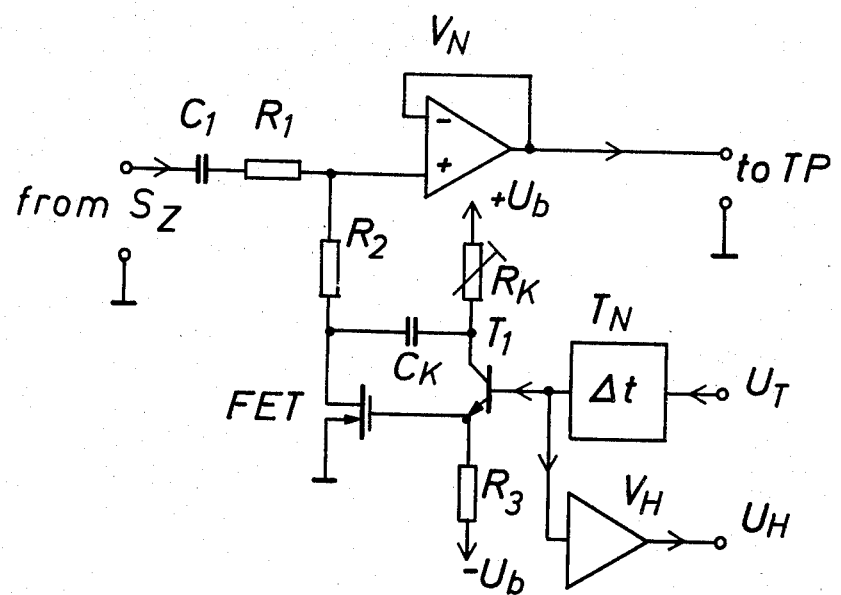

FIG. 6: Circuit diagram of a zero-correction circuit NA as used in FIG. 5 with optional delayed or nondelayed triggering.

Figure 7:
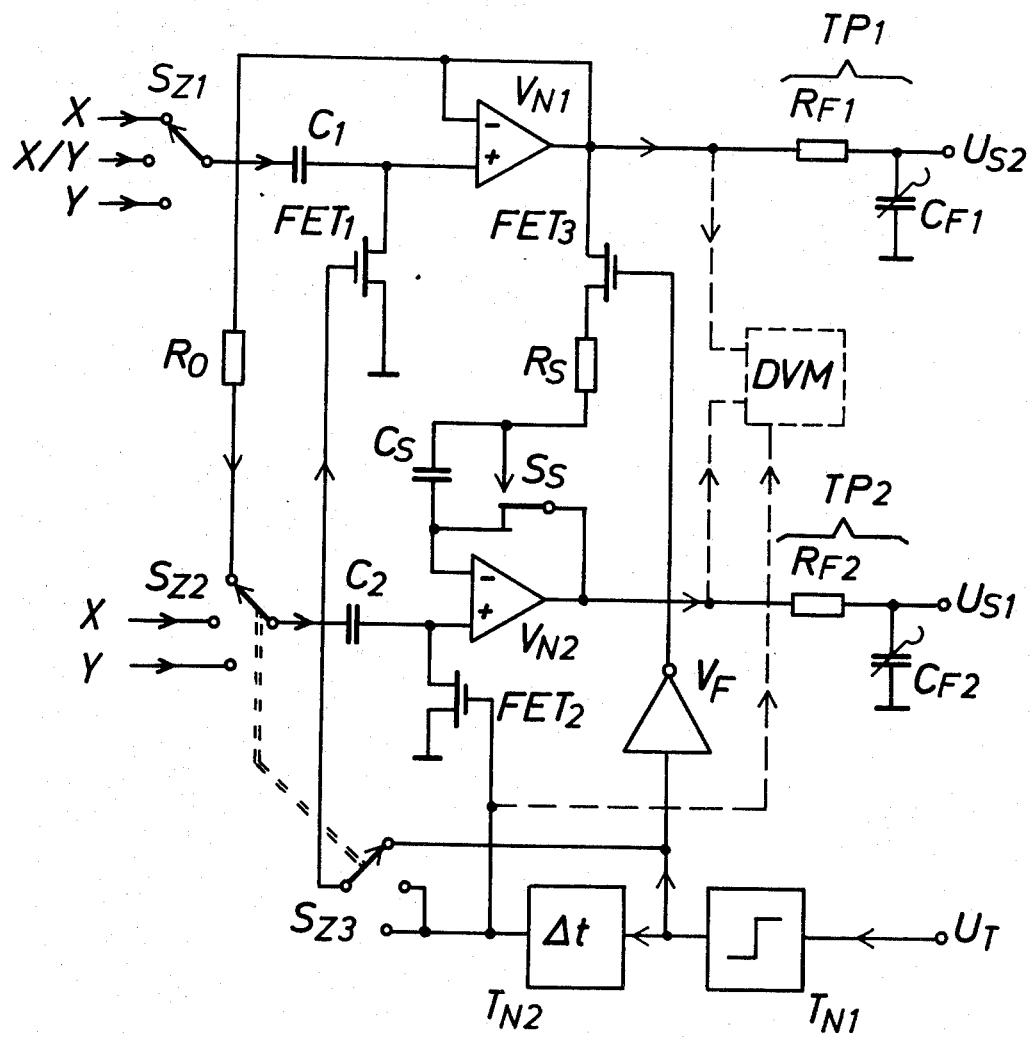

FIG. 7: Circuit diagram of output stage with two zero-correction circuits for independent and cascaded operation.

Figure 8:
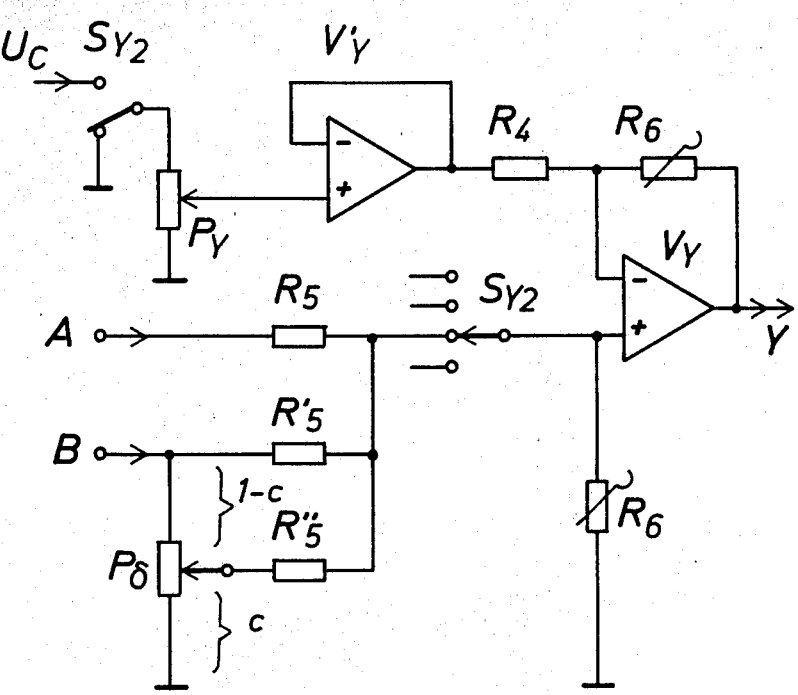

FIG. 8: Circuit diagram of main amplifier $V_y$ with correction for the large-aperture error of polarimetric measurements.

Figure 9:
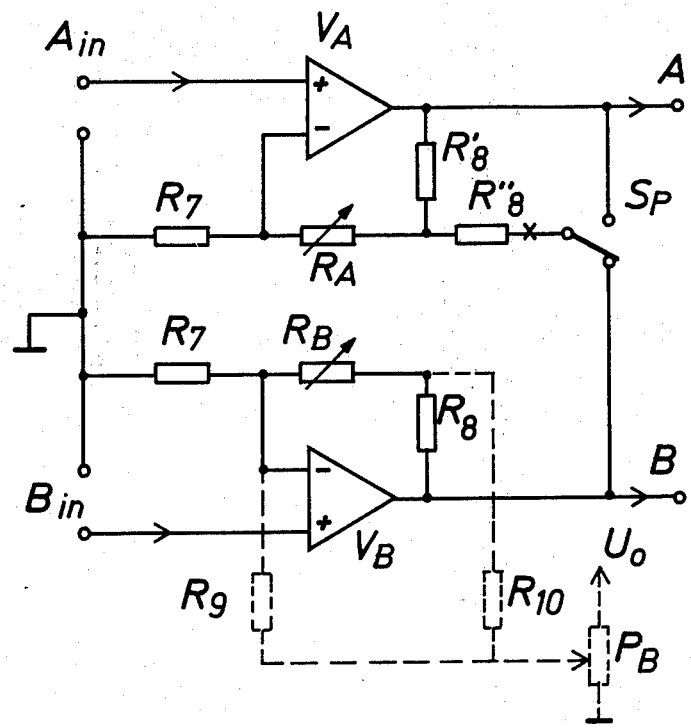

FIG. 9: Circuit diagram of input amplifiers $V_A$ and $V_B$ with alternative correction of the large-aperture error.

Figure 10:
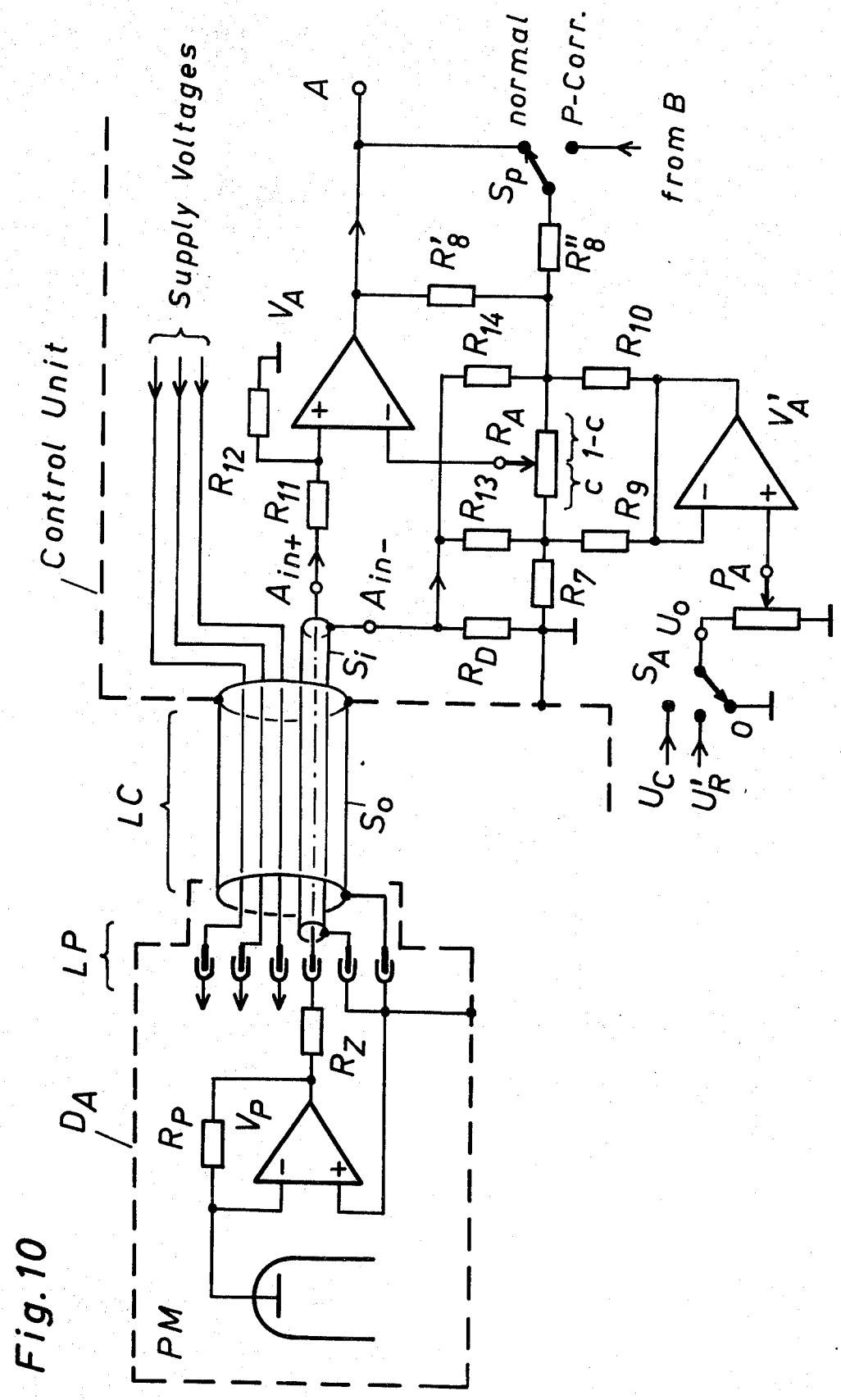

FIG. 10: Circuit diagram of improved input amplifier $V_A$ and connections between the control unit and photodetector head $D_A$.

The high-voltage discharge circuit for producing the temperature-jump and the power supply units for the light source, for the discharge circuit, and for the optoelectronic equipment of the apparatus are not shown.

The optical arrangement of the apparatus is shown in FIG. 1. For a light source Q, high-pressure lamps with mercury and/or xenon filling and a power of 200 Watts or more may be used emitting light in the UV and in the visible range. For measurements of absorption in the visible range, a Quartz-iodine-tungsten lamp may also be used. The light is focused onto the entrance slit of a monochromator M by a condensor lens or lens combination $L_1$. For most applications it is preferable to use a grating monochromator with an aperture ratio of 1:35 or better and a dispersion of 3 nm/mm. The grating is fully illuminated by a field lens $L_2$. Exposure of the monochromator, the sample and the photodetectors to light can be avoided between measurements by means of a light shutter V.

The monochromator exit slit is imaged onto the sample chamber of the measuring cell Z to form a first light path therethrough by a collimator lens $L_3$ (e.g. $f = 100$ mm) and a focusing lens $L_5$ (e.g. $f = 75$ or $100$ mm) that provide an image ratio of 1:1 or less. The position of one of these lenses is axially adjustable to correct for the chromatic error of the focusing point. A collecting lens $L_6$ (e.g. $f = 50$ mm) is used to focus the transmitted light onto the cathode of the absorption photodetector $D_o$ which should have a high cathode current capability (e.g. a photodiode or a side illuminated photomultiplier such as the well known 1P28 of RCA or similar phototubes of other manufactures). For fluorimetric measurements without simultaneous measurements of absorption the lens $L_6$ can be replaced by a concave mirror S, thus doubling the light intensity in the sample cell. The fluorescence light emitted from the sample is collected on both sides of the excitation light path in a second light path by means of a lens combination ($L_7$ or $L_8$ respectively, together with one spherically ground window on each side of the sample cell Z) and brought onto the photocathodes of the fluorescence photomultipliers $D_A$ and $D_B$ after passing through the filters $F_A$ and $F_B$. The photocathode of these multipliers should have a high quantum yield in the ultraviolet and the visible range and optimum homogeneity, esp. freedom from orientation effects. The cathode current capability may be lower than for the detector $D_o$ (e.g. 9558Q or 9817Q of EMI or similar with end-on trialkali-cathode, the so-called S-20 UV type). Part of the primary light is brought onto a reference photodetector $D_C$ by means of a beam splitter T, e.g. a thin fused silica plate, and a collecting lens $L_4$ (e.g. $f = 150$ mm). The reference photodetector $D_C$ should have the same specifications as the absorption photodetector $D_o$. The fluorescence of highly absorbing samples can also be measured by the front-on technique if the beam splitter T is replaced by a dichroic mirror and the fluorescence photomultiplier $D_A$ and the filter $F_A$ are moved to the left positions (indicated by dotted lines). All the lenses, the beam splitter T and the windows of the sample cell Z are made of high-grade strain-free fused silica (e.g. the material known commercially as Spectrosil).

For measurements of fluorescence polarization a polarizing prism P is inserted in the primary light path on the right- or left-hand side of the collecting lens $L_5$ (e.g. a Glan-Thompson or a Glan air calcit prism). As analyzers $F_A'$ and $F_B'$ in the emission light path UV-transmitting polarizing foils are preferred (e.g. Kasemann Polarex types KS-W68 and P-UV 2 or Polacoat type UV 105). The mountings of the polarizer P and the analyzers $F_A'$ and $F_B'$ can be rotated. They have stop positions at 0° and 90°, and at 35.0° or 54.7° respectively.

All optical elements at the right-hand side of the monochromator can be enclosed in a sample cell compartment to which the photodetectors $D_o$, $D_A$, $D_B$, and $D_C$ are attached by light-tight flanges.

Figure 2:
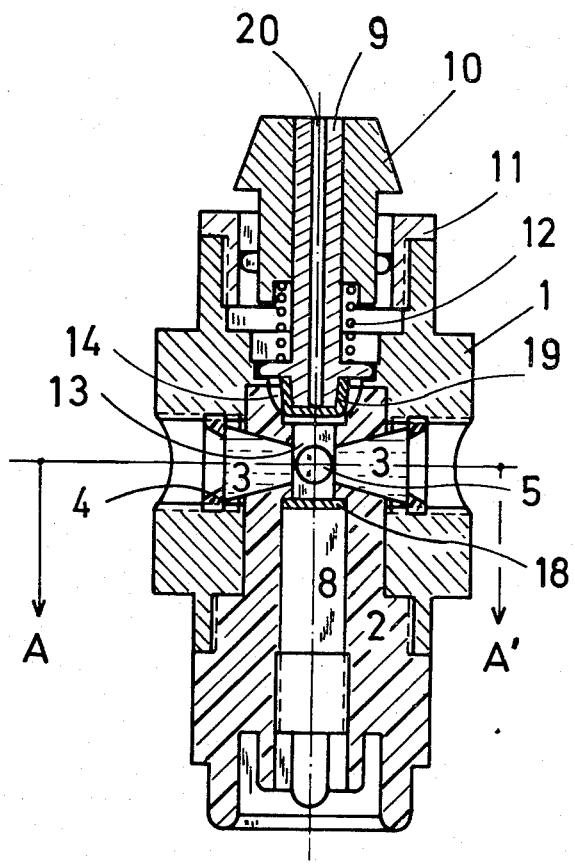
Figure 2:
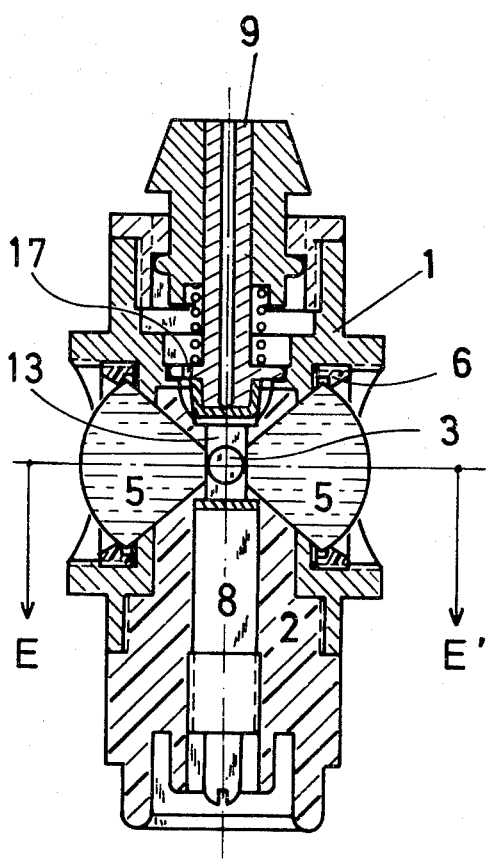
Figure 2:
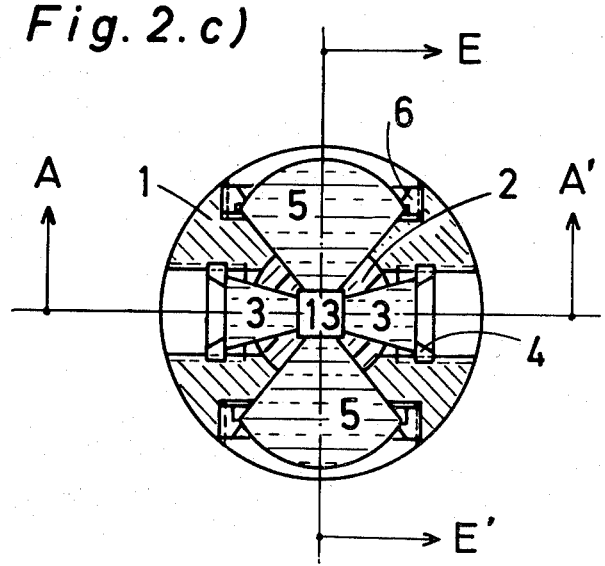
Figure 2:
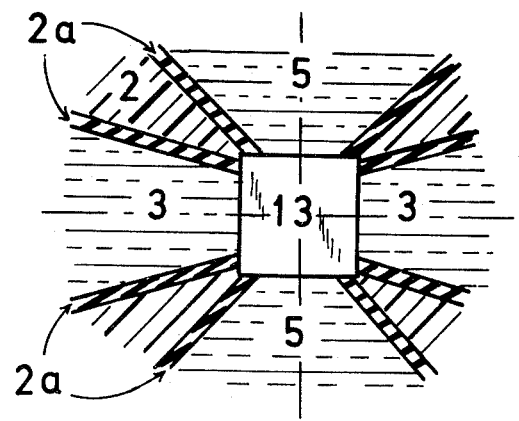
Figure 2:
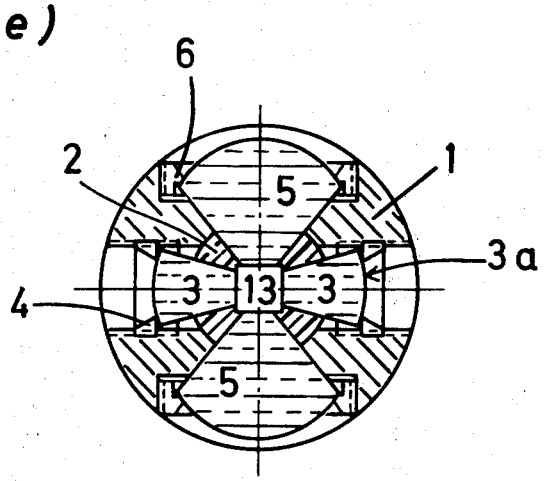
Figure 2:
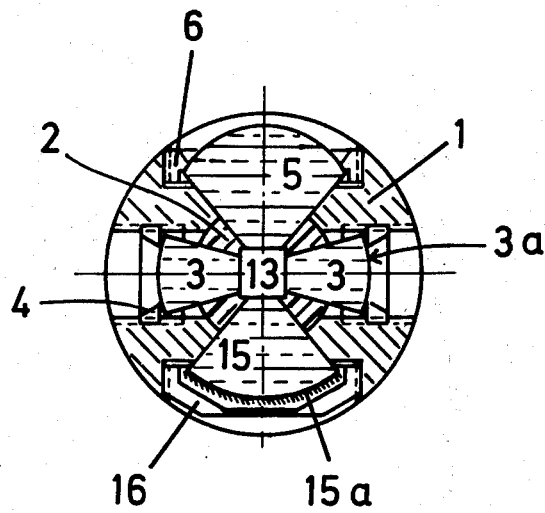

The temperature-jump cell is shown in FIG. 2. FIG. 2a shows a vertical cross section through the axis of the primary or excitation light path, whereas FIG. 2b shows a vertical cross section through the axis of the secondary or emission light path. FIG. 2c is a drawing of the horizontal cross section of the cell. FIG. 2d is an enlarged part of FIG. 2c. FIGS. 2e and 2f demonstrate further modifications.

Besides the maximum yield of the fluorescence light previously mentioned, the design shown in FIG. 2 also fulfills the following requirements:

low intrinsic fluorescence, low stray light and highest possible freedom from strain of the optical elements, small sample volume, high ease of operation for concentration series measurements (titrations) without loss of substance.

The body of the sample cell consists of an outer shell of stainless steel 1 and a core 2 made of PTFE ("Teflon"), black polyacetal resin (e.g. "Dynal" or "Delrin") or a similar material. From below it shows the profile of a high voltage insulator 7. As an alternative the whole cell body can be machined out of one piece of insulating material. The conical cell windows in the excitation light path 3 and in the emission light path 5 have inner diameters of 6 mm e.g., and preferred cone angles, relative to the axis, of 15° and 40°, respectively. They are fixed by mounting rings 4 and 6 which serve also as entrance and exit diaphragms. Special attention has been paid to the different coefficients of thermal expansion. In order to obtain the highest possible freedom from mechanical strain and, at the same time, an optimal tightness the windows are inserted with a solvent-resistant visco-elastic adhesive 2a; preferably with a polymerizing silicone rubber (shown in FIG. 2d in an unscaled and rather exaggerated representation). This is in contrast to the earlier manufacturing procedure where the cones had been greased and then pressed into the cell body. For further improvement, the mounting rings 4 and 6 are underlayed by rubber O-rings. The adhesive is dyed black in order to eliminate any light reflections from the conical walls and any fluorescence of the adhesive material. The same or a similar sealing compound is used for insertion of the lower cell electrode 8 to which the high voltage pulse is applied. A plate of noble metal 18 (gold or platinum) has been soldered onto the top of this electrode as the effective material. The upper electrode 9 is grounded and is covered underneath with a cap 19 of the same noble metal. The electrode shaft has been provided with a blind hole 20 for insertion of a temperature sensing probe.

The sample cell is inserted into a cell holder HZ (FIG. 1) by means of a screw ring or a similar device. Temperature control is done via the cell holder. The cell chamber 13 is square in cross section, e.g. 7 × 7 mm. Consequently, the sample volume of the present construction is approximately 0.7 cm$^3$. A semi-spherical auxiliary volume 14 is provided above the cell chamber together with a hole 17. The upper electrode 9 can be removed from the cell by means of a spring-loaded bayonet socket 10, 11 and 12. Thus, in contrast to known cell constructions, the cell can be opened for adding substances for titration, without removing the cell itself from the holder. This is especially useful for fluorimetric measurements where only very small additions of substance from a microliter syringe are needed. Known cell constructions with special filling bores do not guarantee such accurate titrations or thorough mixing of the sample solution.

Spherically ground conical cell windows have already been used for a fluorescence temperature-jump apparatus. Additional lenses may be used at the cell windows, but no indication is made about their function, dimensioning, and arrangement (G. Czerlinski, Rev. Sci. Instr. 33, p. 1184 (1962)). Four identical cell windows have been used for excitation and emission. This, however, complicates the optimization of the cell with respect to the optical efficiency and, as will be shown below, also with respect to the stray light characteristics.

In contrast to this earlier construction, the sample cell of the new apparatus has a very different dimension in each light path. The free aperture of the excitation windows 3 has been chosen so that the focused light, supplied by a monochromator with a large aperture ratio (e.g. 1:3.5) and by the corresponding optics, can freely pass through the cell without waste of space. A considerably larger conical angle will then be available for the emission windows 5. Furthermore, the inner diameters of the excitation and the emission windows can exceed 80 percent of the horizontal dimensions of the cell chamber, without loss of mechanical stability. For a given sample volume, the light gathering power of the cell is thus maximized. If a larger sample volume is admitted, the inner diameters of the windows can also be larger, e.g. 8 mm for a sample volume of 2 cm$^3$, which gives an improved light gathering power.

The unique performance of the new apparatus is obtained by combining the spherically ground emission windows 5 with additional lenses $L_7$ and $L_8$ in the cell holder very close to the emission windows. This combination has been calculated as a complete optical system and is shown in detail in FIG. 3. The radii of curvature of the lens system are, e.g., $\sigma_1 = 16.2$ mm for the cell window 5, and $\sigma_2 = 23.4$ mm for the lens $L_7$ and $L_8$ (the latter is not shown in FIG. 3). The distance of the centers of curvature from the center of the cell are $a = 8.8$ mm and $b = 18.0$ mm. With a refractive index of $n = 1.5$ for fused silica and $n = 1.33$ for the solvent (water), the focal point of this immersion lens system lies just in front of the center of the cell. The numerical aperture is approximately 0.75.

The light emitted from the center of the cell passes through the filters $F_A$ and $F_A'$ in slightly convergent, nearly parallel rays. Since the dimensions of the lens system are large compared to the dimensions of the cell chamber, an almost parallel light path is also obtained for light emitted by other volume elements within the cell chamber. The free aperture of the lens $L_7$ has a diameter of approximately 40 mm that fits the effective cathode diameter of a 2-inch photomultiplier $D_A$. This adaptation and the nearly parallel light path allow a larger distance between the measuring cell and the photomultiplier, which simplifies the electrical screening. By an appropriate selection of this distance (e.g. 15 cm) the interference of electro-luminescence effects (which sometimes appear during the high-voltage discharge at the cell electrodes) can be avoided, too. In earlier constructions these effects disturbed the fluorescence measurements considerably.

Improved stray light characteristics can be obtained if the lens system in FIG. 3 is modified as shown in FIG. 4 by insertion of a third lens $L_7'$. The focal length of $L_7'$ should be equal to, or larger than, the focal length of the lens $L_7$. This triple lens system forms an enlarged image of the cell volume in the space between the lens $L_7'$ and the photocathode. From this image the volume elements of interest are selected by use of one or two diaphragms $E_1$ and $E_2$. As an example, stray light emitted from the edges of the excitation and/or the emission windows, can be suppressed. In the arrangement shown in FIG. 4, the entrance pupil of the left cell window 5' is imaged on the diaphragm $E_1$ whereas the entrance pupil of the right cell window 5 is imaged on the diaphragm $E_2$. Since the image ratio is different in both cases, diaphragms with different apertures are used. The diaphragm $E_2$ can be omitted if the diameter of the diaphragm required corresponds to the diameter of the photocathode itself. It may be useful to coat the surfaces of the lenses $L_7$ and $L_7'$ (e.g. for the fluorescence spectral range of 320 to 500 nm which is of special interest for biochemical studies). Correspondingly to $L_7'$, a lens $L_8'$ with the corresponding diaphragms belongs to the photomultiplier $D_B$ which is not shown in FIG. 4.

To optimize the spectral efficiency, cut-off filters should be used as emission filters $F_A$ and $F_B$ which cut off the short-wave excitation light and transmit the longer-wave emission light. This is a well known method for obtaining the integral light intensity of the fluorescence emission band. With the new instrument measurements of fluorescence intensities are normally performed with both photomultipliers $D_A$ and $D_B$ in parallel and equal filters $F_A$ and $F_B$ (by using the summing channel Y in FIG. 5). The signal-to-noise-ratio will thus improve by a factor of $\sqrt{2}$. In emission light paths according to FIG. 3, the actual improvement has been found to be even higher. Some light which is normally lost by reflexion from the end-on photocathodes is reflected back through the sample cell and contributes to the useful light intensity.

It is also possible to use different filter $F_A$ and $F_B$ in order to separate the emission bands of different chemical species. An optimum light output can be obtained by using dichroic mirrors as wide-band interference filters that reflect the unpassed light back to the opposite channel. The characteristics of non-available passband filters can be simulated by using different cut-off filters $F_A$ and $F_B$ and by forming the difference of the two measuring signals (utilization of the differential channel X in FIG. 5 which is mainly provided for measurements of polarization).

IMPROVED VERSION OF THE SAMPLE CELL

It has been found that the stray light characteristics of the sample cell itself are highly dependent on the image quality of the excitation light path in the cell and especially on the form of the excitation windows. A reflection of about 4 percent occurs at the back of the exit window. (Right-hand window 3 in FIGS. 2a and c. Application of broad-band antireflex coating is difficult in UV.) Part of the reflected light enters the emission windows 5 and thus contributes to the stray light in the emission light path. A similar reflexion occurs at the front of the entrance window if the spherical mirror S is used in FIG. 1. For lens-ground windows with an unfavourable radius of curvature, as in the case of the above mentioned temperature-jump cell with four identical windows, the stray light is considerable and becomes a limiting factor at low concentrations. Windows which are face-ground on both sides as shown in FIGS. 2a and c have proved to be far less critical in this respect. However, improved stray light characteristics can be obtained by lens-ground windows if the radius of curvature is approximately equal to or slightly larger than the distance from the vertex to the center of the cell. By means of such a spherical lens surface 3a (in which the focal point almost coincides with the center of the cell) the light is reflected back to the cell chamber with imaging quality, thus contributing to the effective primary light.

A cross section of this version is shown in FIG. 2e. The optimal radius of curvature depends on the thickness of the excitation windows. If the thickness equals two times the distance of the windows, the inner surface of the opposite window should be imaged on itself. If the thickness is very large, the center of the cell should be imaged in itself. A larger thickness than shown in the drawing is recommended, also in case of face-ground excitation windows.

FIG. 2f shows a sample cell with only three windows which has been designed for simpler apparatus where only one emission detector is used and measurements of fluorescence polarization are not provided. One emission window 5 of FIGS. 2b to e is replaced by a cone of fused silica 15 metalized on its spherically ground outside 15a. The radius of curvature of the reflecting surface 15a should be such that the center of the sample cell is imaged in itself. Instead of a mounting ring 6, a cover 16 is used. Compared to a three-window cell without the reflector, the reflector improves the light efficiency almost by a factor of 2.5 because the light which is normally lost by the reflectance of the end-on photocathode is reflected back to the cathode.

The constructions of windows, sample cells, and lens systems as described in FIGS. 2 to 4 prove to be useful for other apparatus for reaction kinetic measurements which are not discussed here, such as for flow techniques a.o.

OPTO-ELECTRONIC CONTROL UNIT

FIG. 5 shows the block diagram of an opto-electronic control unit corresponding to the optical arrangement shown in FIG. 1. This control unit is organized as an analog computer and based on operational amplifier techniques (summing and subtracting, continuously and stepwise variable gain factors, electronic division). The circuit shown is provided with two inputs $A_{in}$ and $B_{in}$ which can be connected to two photodetectors in the primary and/or in the secondary light path, e.g. to $D_A$ and $D_B$. Input $C_{in}$ is connected to the reference detector $D_C$. For photodetectors photomultiplier circuits with dynode switching are used because of the unconventionally high light intensities in both light paths. For the photodetectors $D_o$ and $D_C$ vacuum or semiconductor photodiodes can be used, too. The photodetectors are incorporated in individual photodetector heads, provided with current-to-voltage converters, and connected to the control unit by multi-lead cables.

INPUT AMPLIFIERS

Each of the input amplifiers $V_A$, $V_B$ and $V_C$ has a continuously adjustable gain control for setting a normalized signal A, B, and C, respectively. The gain variation may be χ5 to cover the signal jumps when switching the photodetector dynodes. Amplifiers $V_A$ and $V_B$ are provided with offset controls $P_A$ and $P_B$ that are normally switched off (potentiometer voltage $U_0 = 0$). At low light intensities, these offset controls may be used either for dark current compensation (where $U_0$ is chosen as a constant voltage) or used for stray light compensation (where $U_0$ is proportional to the reference signal C). By applying the compensation voltages directly to the inputs, the amplification of the purified signals A and B can be varied without readjustment of $P_A$ and $P_B$. The amplifier $V_C$ is provided with an additional RC-low-pass filter TP', with selectable time constants in the microsecond and lower millisecond range, which is used for fast measurements of absorption in order to give lower photon noise of the reference signal. This is especially powerful in comparative measurements of fluorescence and absorption at low sample absorbance. Schematically drawn as an separate circuit, this lowpass filter is part of the amplifier $V_C$ itself or is followed by a buffer amplifier and does not affect the source impedance at point C.

MAIN AMPLIFIERS $V_X$ AND $V_Y$ AND DIVIDER DIV

Both main amplifiers $V_X$ and $V_Y$ have input selector switches $S_{X1}$ and $S_{Y1}$, calibrated offset controls $P_X$ and $P_Y$ working on their inputs with switches $S_{X2}$ and $S_{Y2}$, and selectable gains of, e.g., 1, 2, 5 and 10. The differential amplifier $V_X$ can be switched to give signals A, B, A-B, or B-A. Offset control $P_X$ can be connected to the reference signal C, to the output of amplifier $V_Y$, or switched off. The summing amplifier $V_Y$ can be switched to give signals A, $(A+B)/2$, $(A/2)+B$, or B. Offset control $P_Y$ is connected to C or switched off. In order to obtain the quantity X/Y, both amplifier outputs can be connected to a fast electronic divider DIV (e.g. using transistors in a current-ratioing circuit). The division modes X/C and Y/C are also provided (not shown). By means of a relay, the divider is switched off by a threshold detector $T_Y$ if the denominator becomes too small, e.g. if the light shutter V is closed in FIG. 1.

MEASUREMENTS OF FLUORESCENCE POLARIZATION AND ORGANIZATION OF ELECTRONICALLY PERFORMED DIVISION

The positions of switches shown in FIG. 5 refer to measurements of the degree of polarization which is defined as $$p = (I_\| - I_\perp)/(I_\| + I_\perp) \tag{1}$$

$I_\|$ and $I_\perp$ are the intensities of the fluorescence light polarized parallel and perpendicular to the excitation light, respectively. The preferred arrangement of the excitation and of the emission light path in FIG. 1 is in the horizontal plane. Thus the polarizing prism P in the excitation light path is orientated vertically for these measurements. The analyzing filter $F_A'$ is also vertically orientated and the analyzing filter $F_B'$ is horizontally orientated in the emission light path. Thus, $A \sim I$ and $B \sim I$. (Definitions are based on the orientation of the electric field vectors. Filters $F_A'$ and $F_B'$ are set parallel to each other in order to balance the sensitivity of channels A and B.) The control unit is used with $X = A-B$, X-gain $x1$, $Y = (A+B)/2$, and Y-gain $x2$. If the offset switches $S_{X2}$ and $S_{Y2}$ are both grounded, the divider output gives $$p = (A - B) / (A + B) = X/2Y \tag{2}$$

For more precise measurements the offset control $P_X$ is switched by $S_{X2}$ to the Y-output and adjusted to compensate for the X signal. The degree of polarization can now be read directly from the offset dial. Changes of the degree of polarization due to a kinetic experiment are obtained as $$\delta p = p - p_o = \frac{(A-B) - p_o(A+B)}{A + B} \tag{3}$$

where $p_o$ is the compensated static value. $X = B-A$ is used if $p$ is negative.

Measurements of polarization based on the fluorescence anisotropy $$r = (I_\parallel - I_\perp) / (I_\parallel + 2I_\perp) \tag{4}$$

are very similar except that $Y = (A/2)+B$. This quantity gives the same information as the degree of polarization but it can be more easily handled when evaluating data on a molecular basis.

For optimum sensitivity in measurements of small differential effects, the X-gain is switched to a higher value, e.g. $x5$ or $x10$, so the complete nominator of eq. (3) is multiplied by a constant factor prior to division. This procedure is mathematically equivalent to a division of $A-B$ by $A+B$ followed by an offset compensation and subsequent amplification. Electronically, however, the described procedure is far superior because the electronic error voltages of the divider, i.e. noise, thermal and temporal instabilities, and linearity errors, have far less influence if the differential signal level is increased first. This is of special interest in kinetic measurements because of the limited accuracy and noise characteristics of fast divider circuits. The same technique is applied, e.g., when measuring fluorescence intensity changes corrected for the inner filter effect (see below).

MEASUREMENTS OF FLUORESCENCE QUANTUM YIELD

Measurements of fluorescence light intensities independent on the orientation of molecules and thus independent of fluorescence polarization must be based on the quantity $I_\parallel + 2I_\perp$, where the ratio 1:2 corresponds to the intensity ratio of components $I_\parallel$ and $I_\perp$ obtained by integration over the total sphere. $I_\parallel + 2I_\perp$ is a measure of the fluorescence quantum field. If the polarizer P and the analyzing filters $F_A'$ and $F_B'$ are in the same position as before, this quantity is obtained by the function $Y = (A/2)+B$. Offset control $P_Y$ is connected to C for measurements of signal changes. The analyzing filters can also be used either in preferred angular positions of 54.7° with respect to the vertical axis, or they can be omitted and the polarizing prism P rotated from the vertical position to an angular position of 35.3°. In both cases, signals A and B can be used separately in channels X and Y, or processed with $Y = (A+B)/2$. Offsets $P_X$ and $P_Y$ are connected to C. Angular stop positions of 53° instead of 54.7° are provided in the emission light path for correction of the large aperture error dealt with below.

OUTPUT STAGE

The signal obtained at the outputs of the divider and main amplifiers $V_X$ and $V_Y$ can be chosen by a selector switch $S_Z$ and connected to a zero-correction circuit NA that is controlled by an optionally non-delayed or delayed Trigger $T_N$ and followed by a variable RC-lowpass filter TP for optimum filtering of noisy signals. For simultaneous measurements of absorption and fluorescence, or of different fluorescence emission bands in channels A and B connected to $V_X$ and $V_Y$, two identical output stages are provided one of which is shown in FIG. 5. The construction of the output stages will be further discussed in FIGS. 6 and 7.

METER CIRCUIT AND OVERLOAD INDICATOR

For the adjustment and amplitude control of the signals, a digital or analog voltmeter can be switched by a meter selector switch to any point marked by a circle in FIG. 5: input signals $A_{in}$, $B_{in}$ and $C_{in}$, adjusted signals A, B and C, combined signals X and Y, and the divider output X/Y. Measurements of the static signals, especially of $A_{in}$, $B_{in}$ and $C_{in}$ when performing titrations, have been found to be essential for correct analysis of the kinetic data. On the other hand, setting of normalized adjusted signals A, B and C is much improved by connecting small differential analog meters $M_A$, $M_B$ and $M_C$ between points A, B and C and a reference voltage where $U_R$ may be either equal to $U_C$ or a fraction thereof or be constant, and $U_{R'}$ is constant. All of the above mentioned signals are controlled by an overload indicator that shows whether any value is out of its proper range. Thus, incorrect settings are easily recognized and nonlinearities are strictly avoided. (Meter selector switch and overload indicator are not shown.)

EXTENSIONS

The diagram of the control unit shown in FIG. 5 can be extended by the following components:
   a fourth input amplifier for simultaneous connection of all photodetectors shown in FIG. 1,
   additional main amplifiers, similar to the amplifier $V_X$ and $V_Y$,
   additional dividers and especially, additional output circuits NA and TP, for multichannel operation and simultaneous measurements of all spectrophotometric parameters of interest, e.g. absorption, fluorescence intensities, and fluorescence polarization, — or absorption, and fluorescence intensities at different emission wavelengths.

This extension is especially useful for correction of the inner filter effect of fluorescence signals due to the finite absorbance of the sample. It can be shown that in relaxation experiments an appropriate correction can be obtained by dividing the fluorescence signal change by the arithmetic mean of the normalized reference signal C and the normalized signal of the absorption detector $D_o$. Therefore, one main amplifier should give the sum of both of these signals. The inner filter effect will then be largely suppressed and the quantitative evaluation of signals facilitated.

Another extension deals with digital control and data processing of the apparatus by a digital computer. The outline of the optoelectronic control-unit shown in FIG. 5 is highly suitable for computer controlled operation. The setting of normalized signals A, B and C is especially suited to computer controlled operation. The following additions or modifications have to be made: All signal points marked by a circle in FIG. 5 ($A_{in}$, $B_{in}$, $C_{in}$ etc.) are connected to a multiplexing MOSFET-switch or a similar device and a medium speed digital-to-analog converter for the measurement of static signals prior to each kinetic experiment. For the gain adjustment of the input amplifiers $V_A$, $V_B$, and $V_C$, multiplying digital-to-analog converters are arranged in the feedback loop of these amplifiers. Multiplying digital-to-analog converters can also be used as offset controls $P_A$, $P_B$, $P_X$ and $P_Y$ instead of manual potentiometers for balancing of the offset voltages. Semiconductor or relay switches may be used for the selector switches $S_{X1}$, $S_{X2}$ etc., in the feedback networks of the main amplifiers $V_X$ and $V_Y$ for setting the gain factors, and also in the reference channel for setting the time constant of the lowpass TP'. All of these adjustments need rather slow control operations where a few milliseconds may be sufficient. The digitally set gain factors, offset voltage division factors etc. will be kept by latch-circuits. Further modifications will depend mainly on the available A/D-conversion and data storage system and its capacity. An amplitude resolution of at least eight bits and a sampling rate of 1 $\mu$sec or less are needed for temperature-jump measurements. If the amplitude resolution is 10 bits or more the delayed triggering operation of the zero-correction circuit NA can be omitted, thus simplifying the control-unit. Division and filtering of the output signal can be performed digitally, thus omitting the divider DIV and a digital control circuit for the lowpass TP. Each main amplifier which is connected for measuring a differential signal must have its own zero-correction circuit NA. The divider can also be omitted if an A/D-converter is used without an internal reference voltage and the denominator voltage is applied as the reference source for A/D-conversion.

In order to obtain as much information as possible, the computer controlled version of the apparatus should be provided with the above mentioned fourth input amplifier, additional main amplifiers etc. For alternative manual and computer controlled operation, the most important gain and offsets controls may also be provided for manual operation.

ZERO-CORRECTION CIRCUIT NA (FIG. 6)

Basically, this circuit is a high-pass equivalent of a sample-and-hold circuit, modified for the special requirements of relaxation experiments using fluorescence detection. Already described circuits are more complex and/or less versatile for this purpose. The one described in FIG. 6 consists of a buffer amplifier $V_N$ with a high impedance FET-input (input current e.g. 1 pA), a hold capacitor $C_1$ with a low leakage current, a resistance $R_1$ in series with the capacitor, and a resistance $R_2$ in series with a field effect transistor FET which works as an electronically controlled switch between the amplifier input and ground (e.g. a p-channel enhancement MOSFET-transistor with an on-resistance $R_F \leq 150$ ohm). This transistor is normally in the on-state. At the start of the chemical experiment a gate voltage $U_T$ is applied to the trigger $T_N$. Depending on the trigger delay time $\Delta t$, which may be zero or any finite value, the transistor is switched to its off-state either undelayed or delayed. A gate signal coupling transistor $T_1$, resistors $R_3$ and $R_K$, and a small capacitor $C_K$ are provided to produce an electric charge pulse to compensate for a capacitive switching pulse which occurs at the upper electrode of the field-effect transistor due to its gate electrode capacitance (e.g. $C_K \approx 10$ pF, $R_K \approx R_3/3$).

If the transistor FET is in its on-state the circuit of FIG. 6 works as a differentiating circuit with the "settling time constant"

$$\tau_s = C_1(R_1 + R_2 + R_F). \tag{5}$$

If the transistor is in its nonconducting off-state the time constant is switched to a very high value (e.g. $10^4$ sec) and any signal change that occurs at the input of the circuit is transferred to its output and thus to the lowpass filter TP.

There are three different operational modes depending on the delay time $\Delta t$ and on the size of the elements $C_1$, $R_1$ and $R_2$. Some typical data are listed in Table I. The delay time $\Delta t$ may be switched in steps of 1: $\sqrt{2}$. $C_1$, $R_1$ and $R_2$ are switched together with the operational modes and with the delay time ranges. If similar circuits are used in other kinetic apparatus designed for longer or shorter time intervals, the values of $\Delta t$ and $\tau_s$ can be chosen accordingly.

Table I

| | Function | $\Delta t_{ms}$ | $\tau_{sms}$ | $C_1 \mu_F$ | $R_{1k}\Omega$ | $R_{2k}\Omega$ |
|---|---|---|---|---|---|---|
| (1) | Drift-filter | 0 | 5 | 2.2 | 0 | 2.2 |
| | ", simplified | 0 | 1 | 2.2 | 0.33 | 0 |
| (2) | Automatic zero-suppression | 0.01..0.1 | <0.01 | 0.03 | 0 | 0 |
| | | 0.1..1 | 0.03 | 0.1 | 0.15 | 0 |
| | | 1..10 | 0.15 | 0.33 | 0.33 | 0 |
| (3) | Short-circuiting device with drift-filter | 0.01..0.1 | 15 | 2.2 | 6.8 | 0 |

1. Drift-filter ($\Delta t = 0$)

Because of the very high sensitivity of the new apparatus, it has been found that exact and temporally constant balancing of the static signals is impossible. Even the smallest thermal and photochemical instability of the sample solution will cause a measurable drift-effect. Frequent and cumbersome rebalancing is avoided by using the zero-correction circuit in its nondelayed drift-filter mode. Prior to measurement the FET is conducting, and drift effects are suppressed by a settling time constant $\tau_s$ of the order of 1 ms. As soon as the relaxation experiment has been started the time constant is switched to an extremely high value of up to $10^5$ sec which is effectively infinite compared to the fast signal changes due to the chemical processes. The corrected signal starts from an exact zero baseline level. The resistor $R_2$ blocks noncompensated switching pulse effects at the FET completely and avoids interferences arising from slightly delayed opening of the FET. In simplified circuits the resistor $R_2$ can be omitted or replaced by a smaller resistor $R_1$ of, e.g., 330 ohms supposed that the opening delay is of the same order as the lag-time of the input and the main amplifiers and that the switching transients remain small compared to the amplified signals. A finite resistor $R_1$ then acts as a protection resistor to the FET and to the main amplifier or the divider output. This is appropriate with respect to operating errors. Because of the large size of the capacitor $C_1$, large charge currents occur if the gate voltage $U_T$ is not applied, especially AC-currents if the photodetectors are exposed to room light.

2. Automatic zero-suppression (preferred range $\Delta t = 10 \mu s..10$ ms)

Signal drifting prior to measurements is suppressed in a similar way as in the drift-filter mode. The settling time constant $\tau_s$, however, has been chosen to be smaller than the trigger delay time $\Delta t$. Thus, fast signal changes occurring during the time $\Delta t$ are largely suppressed. This is important for measuring slow relaxation effects of small amplitude that follow larger fast effects and have to be displayed on an oscilloscope at full size. Such effects are typical in fluorescence temperature-jump measurements because of the temperature dependence of quantum yields that gives large instantaneous signal changes. The upper limit of $\tau_s$ is given by $\Delta t$. The lower limit is determined by the optical noise superimposed on the effective signal. Too small values of $\tau_s$ lead to uncontrolled fluctuations of the output signal. The lower limit of $C_1$ [that also effects $\tau_s$ according to eq. (5)] is given by the input current of the buffer amplifier $V_N$ and the leakage current of the elements with respect to the size and the time interval of the measured signal. An optimum performance has been obtained by switching the time constant $\tau_s$ together with the delay time $\Delta t$ where the coupling of $\tau_s$ to $\Delta t$ may be closer than indicated in Table I. At short times $\Delta t$ the ratio $\tau_s/\Delta t$ must be larger than at longer times. E.g., $\tau_s$ may vary by a factor of 30 or 100 if $\Delta t$ is varied by a factor of 1000. During the delay time the oscilloscope beam is blanked by a voltage $U_H$ supplied by an auxiliary amplifier $V_H$. A finite value of the resistor $R_1$ gives a well defined settling time $\tau_s$ and reduces precharging of the lowpass filter TP. The maximum value of $R_1$ is limited with respect to the switching transients of the FET, as above mentioned with the drift-filter. $R_1$ can be omitted in simplified circuits with less complete suppression of the switching transients. $R_1$ can also be replaced by a finite $R_2$ for improving the suppression of switching transients.

3. Short-circuiting device with drift-filter (preferred range $\Delta t = 10 \mu s ... 100 \mu s$)

The measuring signal is short-circuited for the set delay time $\Delta t$ with $R_1 >> R_F$ and $R_2 = 0$. This operational mode is useful in measurements of highest sensitivity in order to suppress electroluminescence effects that sometimes occur in the sample cell during the HV-voltage discharge and depend on the chemical system. This mode of operation avoids precharging of the lowpass filter TP and the irreducible transients then introduced. Contrary to the zero-suppression mode, no zero shift occurs because of the very large settling time $\tau_s >> \Delta t$. Relaxation times shorter than the delay time $\Delta t$ cannot be detected in this mode but the amplitudes of fast signal changes can still be measured without distortion after delay. During the delay time the oscilloscope beam is blanked as before.

DOUBLED AND CASCADED ZERO-CORRECTION CIRCUITS

FIG. 7 shows a doubled output stage with two zero-correction circuits and two lowpass filters TP 1 and TP 2 that can be used either for simultaneous measurements of two of the three signals X, Y, and X/Y, as mentioned before, or cascaded for nondelayed and delayed measurements of the same signal. The time constants of TP 1 and TP 2, given by the elements $R_{F1}$, $C_{F1}$, $R_{F2}$ and $C_{F2}$, can be set independently for optimum matching to the measuring time intervals. Two buffer amplifiers $V_{N1}$, $V_{N2}$, hold capacitors $C_1$, $C_2$ (both selected according to Table I), and field-effect transistors FET 1, FET 2 are provided. Resistors $R_1$, $R_2$, $R_3$ and $R_K$ and transistors $T_1$ are not shown in this diagram and shall be chosen as in FIG. 6. Two triggers $T_{N1}$ and $T_{N2}$ are series- or parallel-connected to the gate voltage $U_T$. $T_{N1}$ is nondelayed operated only whereas $T_{N2}$ corresponds to the trigger $T_N$ in FIG. 6. The measuring signals are selected by switches $S_{Z1}$ and $S_{Z2}$. The control voltage of FET 1 can be selected by a switch $S_{Z3}$ coupled to $S_{Z2}$. In the upper position of $S_{Z2}$ and $S_{Z3}$ both zero-correction circuits are cascaded to obtain nondelayed and delayed output signals $U_{S1}$ and $U_{S2}$. With respect to the output current capability of $V_{N1}$ a decoupling resistor $R_o$ of, e.g., 200 ohms can be provided between $V_{N1}$ and $S_{Z2}$.

In many cases where recording the delayed signal $U_{S2}$ is insufficient, however, it is adequate to measure the time course of $U_{S2}$ together with the voltage shift $\Delta U_S = U_{S1} - U_{S2}$ instead of both voltages $U_{S1}$ and $U_{S2}$. The voltage $\Delta U_S$ is kept in the capacitor $C_2$ during measurement. It can be measured by a digital voltmeter DVM connected to the output of the two amplifiers $V_{N1}$ and $V_{N2}$ and controlled by the trigger $T_{N2}$ (in FIG. 7 drawn in broken lines). The voltmeter therefore must have a differential input, controlled start and hold and an adequate A/D-conversion time. The trigger $T_{N1}$ should be provided with a gate pulse prolongation circuit if the voltage $U_T$ can be applied for a shorter time than needed for A/D-conversion (e.g. 100 ms).

In the circuit shown in FIG. 7 any voltmeter can be used for measuring the voltage $\Delta U_S$ instead of the described one if a special storage capacitor $C_S$ is connected between the amplifier outputs by a decoupling resistor $R_S$ and a field-effect transistor FET 3 which is controlled by an inverting amplifier $V_F$ and is conducting during measurements only. After measurement, a pushbutton or a relay contact $S_S$ is switched to its upper position and the voltage $\Delta U_S$ is obtained between the output of $V_{N2}$ and ground. Contrary to the value of $C_2$ in the delayed mode, the capacitance of $C_S$ may be a few microfarads so that $\Delta U_S$ is stored for even longer times without error. The charge time constant, given by $C_S$, $R_S$ and the on-resistance of FET 3, may be of the order of 10 ms.

LARGE-APERTURE CORRECTION CIRCUIT FOR MEASUREMENTS OF FLUORESCENCE POLARIZATION

The large aperture of the sample cell Z shown in FIG. 2 results in a depolarization of the emitted fluorescence light. The effective half-aperture angles, relative to the axis and to the refractive index of water, are approximately 8° with the excitation light path and 34° with the emission light path. With the polarizing prism P in the vertical position and analyzing filters $F_A'$ and $F_B'$ in the vertical and horizontal positions, respectively, the normalized signals A and B are not equal to $I_\parallel$ and $I_\perp$, as assumed in eq. (1), but $$A = (1 - \delta)I_\parallel + \delta \cdot I_\perp$$
$$B = \delta' \cdot I_\parallel + (1 - \delta')I_\perp \tag{6}$$

With the above given aperture angles, $\delta = 8$ percent and $\delta' = 0.5$ percent. Thus, the measurement of the emission component $I_\parallel$ is affected mainly whereas B is still almost equal to $I_\perp$. If the aperture error is neglected, an apparent degree of polarization $p'$ is measured instead of the true degree of polarization $p$:

$$p' = \frac{A-B}{A+B} = \frac{(1-\delta)I_\parallel - (1-\delta)I_\perp}{(1-\delta)I_\parallel - (1+\delta)I_\perp} = \frac{(1-\delta)p}{1-\delta \cdot p} \tag{7}$$

where, as an approximation, the contribution of $\delta'$ is omitted. In order to avoid numerical conversion of the measured data an electronic correction is applied, two versions of which are described in FIGS. 8 and 9.

In FIG. 8 a special coefficient network is used at the input of the main amplifier $V_Y$. An adjustable correction for measurements with cells of different aperture is provided by a correction potentiometer $P_\delta$. With the selector switch $S_{Y1}$, only the connection corresponding to the function $Y = (A+B)/2$ is shown (slider of $P_\delta$ in the upper position). Summing resistors are $R_5$, $R_5'$ and $R_5''$ where $$1/R_5 = 1/R_5' + 1/R_5'' \tag{8}$$

e.g. $R_5'' = 5R_5$, and the resistance of $P_\delta$ is small compared to $R_5''$. $c$ is the voltage division factor of $P_\delta$. $P_\delta$ is calibrated in terms of $$\delta = (1-c)R_5/2R_5'' \tag{9}$$

in order to give the function $$Y = [A + (1-2\delta)B]/2 \tag{10}$$

Resistors $R_4 = R_5/2$ and $R_6$ are used in the feedback loop of the amplifier $V_Y$ for setting the Y-gain as usual. The offset circuit with switch $S_{Y2}$, offset control $P_Y$ and a buffer amplifier $V_Y'$ is switched off. Thus, if the Y-gain is $x2$, the degree of polarization is measured as $$p = \frac{A-B}{A+(1-2\delta)B} = \frac{(1-\delta)(I_\parallel - I_\perp)}{(1-\delta)(I_\parallel - I_\perp)} \tag{11}$$

A more complete correction including the coefficient $\delta'$ in eq. (6) can be obtained by providing a slightly reduced gain with the A-input of amplifier $V_Y$ which can also be made adjustable. This modification is useful if the large aperture error of the sample cell is added to the error due to an incomplete polarization of the analyzing filters $F_A'$ and $F_B'$ which can be corrected by the same circuit.

According to FIG. 9 the correction of the large aperture error can also be performed at the input amplifiers $V_A$ and $V_B$. This is especially useful for correcting alternative measurements of the degree of polarization, of the polarization anisotropy eq. (4), and of the fluorescence quantum yield $I_\parallel + 2I_\perp$. In the circuit shown in FIG. 9, the error component $\delta \cdot I_\perp$ is eliminated by subtracting part of the adjusted signal B from the signal A and then increasing the amplification of the remaining signal $(1-\delta)I_\parallel$ by a factor of $1/(1-\delta)$. Both input amplifiers $V_A$ and $V_B$ have feedback networks with variable resistances $R_A$ and $R_B$ for gain adjustment, and fixed resistors $R_7$, $R_8$, $R_8'$ and $R_8''$ where $$1/R_8 = 1/R_8' + 1/R_8'' \tag{12}$$

and $$\delta = R_8/R_8'' \tag{13}$$

If the switch $S_p$ is in its normal upper position, the gain of the amplifier $V_A$ is $$v = (R_7 + R_8 + R_A)/R_8 \tag{14}$$

In the lower position of $S_p$, the output signal is $$A_{corr} = A_{in} \cdot v \cdot R'_8/R_8 - B \cdot R'_8/R''_8 = \frac{v}{1-\delta}A_{in} - \frac{\delta}{1-\delta}B_{in} \tag{15}$$

where $v \cdot A_{in}$ is the uncorrected signal A. The gain of amplifier $V_B$ is given by eq. (14) when substituting $R_A$ by $R_B$. Values are, e.g., $\delta = 0.08$, $R_8 = 820$ Ω, $R_8' = 891$ Ω, $R_8'' = 10.3$ kΩ, $R_4 = 1.6$ kΩ and $R_A$ and $R_B = 0$ . . . 10 kΩ for $v = 1.5 \ldots 7.5$. The gain of both input amplifiers has to be adjusted with equally orientated analyzers $F_A'$ and $R_B'$ to the same normalized values A and B as before. For adjustment of signal A, the switch $S_p$ must not be set back to its upper position if signal B is adjusted prior to A. Thus, the circuit shown in FIG. 9 can be easily operated.

IMPROVEMENTS:

In FIG. 9 a continuous setting of the large aperture correction similar to FIG. 8 can be obtained by connecting a potentiometer between the output of amplifier $V_A$ and the commutating contact of switch $S_p$ and connecting the resistor $R_8''$ to the slider of the potentiometer (modifications at the point marked by a cross in FIG. 9). In this case eq. (13) applies to the maximum value of $\delta$. E.g., $R_8' = 902$ Ω and $R_8'' = 8.2$ kΩ for $\delta = 0 \ldots 0.10$. For a linear calibration, the potentiometer has to have a low impedance compared to $R_8''$, or it can be followed by a buffer amplifier. A correction of the smaller error coefficient $\delta'$ in eq. (6) can be obtained by providing a similar circuit with the feedback network of input amplifier B.

INPUT OFFSET CIRCUIT

Elements $R_9$, $R_{10}$ and $P_B$ (in FIG. 9 drawn in broken lines with the input amplifier B) show how the above mentioned input offset voltage can be introduced without interference to the gain adjustment procedure. Therefore, the bridge condition is $$R_9/R_7 = R_{10}/R_8 \tag{16}$$

A buffer amplifier can be inserted at the slider of the offset potentiometer $P_B$ in order to obtain a linear calibration. The gain formula (14) becomes slightly modified but eqs. (12) and (13) are not modified.

SCREENING PROBLEMS

Electrical screening between the opto-electronic detection system and the high-voltage discharge circuit is most important in temperature-jump-experiments. When discharging the high-voltage capacitor, the slew rate of the voltage across the sample cell is $dU/dt \simeq 10^{12}$ V/s, and that of the current is $dI/dt \simeq 10^{10}$ A/s. A damping factor $\geq 160$ dB at the opto-electronic system is needed to avoid interferences. This value cannot be safely obtained by conventional shielding. A coaxial design of the discharge circuit is already known. Improved shielding can be obtained by a very compact design of the opto-electronic system. This, however, contradicts the above mentioned arrangement of the photodetectors in individual photodetector heads which is needed for optimal flexibility of the optical design, e.g. for moving the photodector $D_A$ to its left position in FIG. 1. For measurements of fluorescence polarization, it is also important to have the end-on photodetectors $D_A$ and $D_B$ in-line arranged with the emission light path. This results in relatively long cables between the detector heads and the control unit.

Improved suppression of interfering electrical effects has been obtained by the arrangement shown in FIG. 10 that is outlined for the detector head $D_A$ and the input amplifier $V_A$ which is provided with a differential input circuit. On the left side of FIG. 10, part of the photodetector tube PM, a load resistor $R_P$ and an operational amplifier $V_P$ connected as a current-to-voltage converter are shown. The detector head is connected to the control unit by a multi-lead connector LP and a multi-lead cable LC which contains the supply voltage leads and a smaller coaxial cable for the signal voltage connection. Thus, a double screening is obtained. The outer screen $L_o$ connects the casings of the detector head and of the control unit directly. The inner screen $L_i$ connects the differential input $A_{in-}$ to the detector head ground whereas the inner coaxial conductor connects the other differential input $A_{in+}$ to the signal output of the detector head. The resistor $R_Z$ matches the detector head to the characteristic impedance of the coaxial cable of, e.g., 50 or 75 Ω. At the control unit input $A_{in-}$ a damping resistor $R_D$ of, e.g., 15 Ω is provided which can also be series-connected with a capacitor of, e.g., 0.1 μF. Both resistors $R_Z$ and $R_D$ have been found to be useful for damping spurius RF-pick-up produced by the high-voltage discharge, which otherwise could affect the input of the amplifier $V_A$ even if the RF-frequency is too high to be transferred to the control unit output. For frequencies within the pass-band of the control unit the differential input is matched by small capacitors parallel to the resistor $R_{12}$ and with the feedback network of amplifier $V_A$ (not shown in FIG. 10). Thus, a common-mode suppression of 50 dB is obtained for most of the frequency range which adds to the suppression obtained by proper electric shielding.

Various differential amplifier circuits can be used for this purpose. The one shown at the right side of FIG. 10 is a differential version of the non-differential amplifier circuit of FIG. 9. It combines the unique feature of the large aperture correction and the application of the input offset voltage already described with a differential amplifier that needs only one adjustable element with one arm for continuous gain adjustment. Especially, only one high precision amplifier $V_A$ is needed, compared to two of these amplifiers in more conventional circuits. Amplifier $V_A'$ is provided as an offset-generator only and may be a low cost type. Together with eqs. (12) and (13) for the large aperture correction, where $1/R_8 = 1/R_8' + 1/R_8''$, and eq.(16) for the offset circuit, there are the following bridge circuit conditions for correct differential operation:

$$R_7/R_8 = R_9/R_{10} = R_{13}/R_{14} \qquad (17)$$

and $$(R_{11} + R_Z)/R_{12} = R_{13}(1/R_7 + 1/R_9) \qquad (18)$$

For improved gain adjustment the variable resistor $R_A$ of FIG. 9 has been replaced by a potentiometer $P_A$, where $c$ is the voltage division factor. The gain of the input amplifier circuit is then $$v = \frac{R^*}{R_{13}} \cdot \frac{R^* + R_A}{R^* + cR_A} \cdot \frac{R_8 + R^{}}{R^{}}, \qquad (19)$$

where $$1/R^* = 1/R_7 + 1/R_9 + 1/R_{13} \qquad (20)$$

and $$1/R^{**} = 1/(R^* + R_A) + 1/R_{10} + 1/R_{14} \qquad (21)$$

The gain relative to the voltage at the slider of the offset potentiometer $P_A$ is $$v' = (R_{13}/R_9) \cdot v. \qquad (22)$$

For practical reasons one may set $R_7 = R_8 = R_{13} = R_{14}$ and $R_9 = R_{10} = 5R_7$, e.g. $R_7 = 1.5$ KΩ. With $R_Z = 50$ Ω and $R_{11} = 1.5$ kΩ, one has $R_{12} = 1.292$ kΩ. For δ = 0.083: $R_8' = 1.636$ kΩ and $R_8'' = 18$kΩ. A low inductance 10-turn potentiometer of 2 kΩ can be used for $R_A$ which gives $V = 1.25 \ldots 5$ and $v' = 0.25 \ldots 1$.

The design of the input amplifier $V_B$ is identical to $V_A$ except that the resistor $R_8'$ is replaced by $R_8$ and that the switch $S_P$ and the resistor $R_8''$ are omitted. (For modifications, such as continuous adjustable corrections of coefficients δ and δ', see above.) Both amplifiers have offset switches such as $S_A$ with $P_A$ for selecting for $U_o$ either $U_C$, or a constant voltage $U_R'$, or zero. Input amplifier $V_C$ has a differential input, too, and the above mentioned lowpass filter TP', but no offset generator. The connections to the photodetector heads are the same as in FIG. 10. Induced error voltages are largely avoided by the multi-lead cables.

What is claimed is:

1. An apparatus for investigating the course of fast chemical reactions by optical detection, said reactions being initiated in a chemical system under investigation by an external perturbation, said apparatus comprising a first light path for conveying a probing light beam, said first light path comprising a light source, means for monochromatic light filtering, collimating and focusing elements, a beam divider to provide a reference beam and a probing beam, and at least one photodetector, said apparatus further comprising a second light path for conveying a sensing light beam, said second light path intersecting said first light path within a region of intersection, said probing light beam being focused onto said region of intersection, said apparatus further comprising means for supporting a sample cell at said region, said sample cell forming a chamber for holding a liquid sample of said chemical system, said sample cell having two opposite windows and at least one further window, said windows having plane inner surfaces, said two opposite windows being transversed by said first light path and said further window being transversed by said second light path and the cross section of said chamber acting nearly completely as said region of intersection; said further window having a convexly curved outer surface forming a collecting lens, and the cross sectional area of said further window tapering from said lens surface towards said chamber; a further lens element close to said further window positioned in said second light path wherein said further window has a considerably larger aperture angle and a larger refractive power for light rays passing through the center of said chamber as compared to said opposite windows in said first light path, said second light path further comprising at least one photodetector, and means for spectral light filtering of the light in the second light path.

2. Apparatus according to claim 1, characterized in that said further window in said second light path and said additional lens element cooperate in forming an immersion-optical system, whose focus is in a space including the center of said chamber and extending a short distance towards said further window; said lens element being supported by said cell supporting means.

3. Apparatus according to claim 2, wherein the diameter of the entrance surface of said immersion-optical system is essentially equal to the dimension of said chamber in the direction of said first light path.

4. Apparatus according to claim 2, wherein the effective half-aperture angle of said immersion-optical system with respect to the volume of said chamber is 34° approximately, corresponding to a mean numerical aperture of about 0.75.

5. Apparatus according to claim 1, wherein said sample cell has four windows and said second light path comprises two portions, the arrangement of said portions being essentially symmetrical with respect to said first light path, each of said portions comprising its own photodetector.

6. Apparatus according to claim 5, wherein said first light path and each of said portions of said second light path comprise a polarizing optical element, at least one of said elements being mounted to enable rotation by 90° around the axis of the related light path.

7. Apparatus according to claim 1, wherein said sample cell has a lens shaped conical glass body (15) opposite to said further window in said second light path, said glass body having a plane inner surface facing said chamber and a metalized spherical outer surface, the center of curvature of which coincides essentially with the center of said chamber.

8. Apparatus according to claim 1, characterized in that each of said windows in said first light path has a spherical outer surface, the center of curvature of which coincides essentially with the center of said chamber.

9. Apparatus according to claim 8, wherein said curvature is such that light reflected from said outer surface images the inner surface of the respective opposite window onto itself.

10. Apparatus according to claim 1, wherein said windows have conical walls and are mounted in the body of said sample cell by means of a black rubberlike visco-elastic polymer, and by mounting rings that serve as auxiliary entrance and exit diaphragms.

11. Apparatus according to claim 10, further comprising resilent O-rings underlying said mounting rings, said O-rings controlling the mechanical forces excerted onto said conical walls.

12. Apparatus according to claim 1, characterized by first and second electrodes mounted on opposite sides of said chamber, parallel to a plane comprising said first and second light paths, said first electrode being above said plane and mounted by a locking device (10,11,12) which can easily be opened without removing said cell from said supporting means.

13. Apparatus according to claim 1, said first light path further comprising a removable spherical mirror positioned on the side of said sample cell which is opposite to said light source, said mirror essentially imaging the center of said chamber onto itself.

14. Apparatus according to claim 1, said first light path further comprising another lens between said additional lens and said photodetector, wherein said second light path is almost telecentric between said lenses and forms a three-dimensional image of the irradiated chamber volume in front of said photodetector; said image being limited by two area limiting diaphragms ($E_1, E_2$).

15. Apparatus according to claim 14, wherein the photocathode area of said photodetector serves as a second one of said diaphragms.

* * * * *